United States Patent [19] [11] 4,224,238
Nagato et al. [45] Sep. 23, 1980

[54] PROCESS FOR PREPARING TERTIARY ALKYL ISOCYANATES

[75] Inventors: Nobuyuki Nagato, Wako; Taketoshi Naito, Yokohama, both of Japan

[73] Assignee: Showa Denko K.K., Tokyo, Japan

[21] Appl. No.: 30,649

[22] Filed: Apr. 16, 1979

[30] Foreign Application Priority Data

Apr. 18, 1978 [JP] Japan ................................. 53/44833

[51] Int. Cl.$^2$ ........................................... C07C 118/00
[52] U.S. Cl. ................................................ 260/453 P
[58] Field of Search ..................................... 260/453 P

[56] References Cited

U.S. PATENT DOCUMENTS

| | | | |
|---|---|---|---|
| 3,558,684 | 1/1971 | Von Brachel et al. | 260/453 P |
| 3,948,966 | 4/1976 | Inamoto et al. | 260/453 P |
| 4,056,547 | 11/1977 | Tanaku et al. | 260/453 P |
| 4,130,577 | 12/1978 | Nagato et al. | 260/453 P |

*Primary Examiner*—Dolph H. Torrence
*Attorney, Agent, or Firm*—Wenderoth, Lind & Ponack

[57] ABSTRACT

Process for preparing an alkyl isocyanate having the isocyanate group bonded to the tertiary carbon atom of the alkyl group, which comprises reacting the corresponding alkyl halide in a substantially anhydrous condition in the presence of a specified catalyst with an alkali metal cyanate in an aprotic solvent which forms no salt with a hydrogen halide.

10 Claims, No Drawings

PROCESS FOR PREPARING TERTIARY ALKYL ISOCYANATES

This invention relates to a process for preparing an alkyl isocyanate in which the isocyanate group is bonded to the tertiary carbon atom of the alkyl group.

The alkyl isocyanate having the isocyanato group bonded to the tertiary carbon atom of the alkyl group may be represented by the general formula

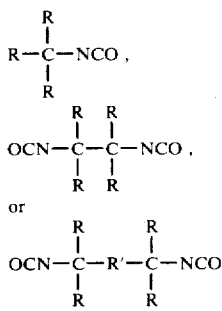

wherein R represents an alkyl group R' represents an acyclic or cyclic alkylene group. Specific examples are (i) tertiary butyl isocyanate and tertiary amyl isocyanate, (ii) 2,3-diisocyanato-2,3-dimethyl butane, and (iii) 2,4-diisocyanato-2,4-dimethyl pentane and 1,4-bis(2-isocyanato-2-propyl)cyclohexane. Such an alkyl isocyanate having the isocyanato group bonded to the tertiary carbon atom of the alkyl group is referred to hereinbelow as "tertiary alkyl isocyanate" for brevity. The corresponding alkyl halide having the halogen bonded to the tertiary carbon atom of the alkyl group is referred to simply as "tertiary alkyl halide".

The tertiary alkyl isocyanates are useful as intermediates for the synthesis of various organic compounds, medicines or agricultural chemicals.

The process for producing the tertiary alkyl isocyanate in accordance with this invention comprises reacting the corresponding tertiary alkyl halide with an alkali metal cyanate in the presence of a specified catalyst. This process will be described in greater detail hereinbelow. Before describing the invention in detail, the prior art and its difficulties are dealt with.

The most common synthetic route to organic isocyanates by the prior art techniques is based on the reaction of the corresponding organic amines with phosgene. However, phosgene is a very toxic substance, and is difficult to handle and particularly to transport safely. Moreover, every measure must be taken to prevent its leakage during storage and reaction operations. This method, therefore, has the defect that the equipment for producing phosgene must be provided at a site adjoining the place of its use. In the case of production of tertiary alkyl isocyanates, another disadvantage is that the starting tertiary alkylamines are also difficult to produce. For example, tert-butyl amine is commercially produced by a method which comprises reacting isobutylene with hydrocyanic acid in the presence of concentrated sulfuric acid in accordance with a reaction known as the Ritter reaction, neutralizing the reaction product with a concentrated aqueous solution of ammonia to form tert-butyl formamide, and then hydrolyzing it with sodium hydroxide to convert it to the amine (e.g., U.S. Pat. No. 2,773,097). The yield obtainable by this method is not entirely satisfactory. Hydrocyanic acid used in this invention is a very toxic substance like phosgene and is undesirable from the viewpoint of safety measure. Moreover this method presents problems associated with the use of concentrated sulfuric acid and the formation of large quantities of by-products such as inorganic salts. Thus, for commercial application, this method is far from being satisfactory.

There are also a method involving the thermal decomposition of α,α-dimethylpropionic acid azide and a method involving the oxidation of α,α-dimethylpropionic acid isocyanide. However, these methods are commercially valueless because the starting materials themselves are not easy to synthesize.

Some other methods are known to produce organic isocyanate compounds, but none of them are satisfactory when applied to the production of the tertiary alkyl isocyanate in accordance with this invention.

Attempts were made to produce organic isocyanates by the reaction of organic halides with alkali metal cyanates. Such a method was considered commercially advantageous over the aforesaid method using phosgene or hydrocyanic acid because the organic halides, especially the chlorides, are relatively easily available and the alkali metal cyanates have very low toxicity as compared with phosgene or hydrocyanic acid and are easy to handle, and particularly, sodium cyanate is commercially available at low cost. Actually, however, this reaction was not as simple as had been expected, and no satisfactory technique has been established up to date. This prior art technique is described hereinbelow in some detail.

It is generally known that the reactivity of an organic halide with an alkali metal cyanate is very poor, and mere mixing and heating of these materials do not induce reaction, and that the desired isocyanate can scarcely be obtained even when the reaction is carried out in a nonpolar or weakly polar solvent such as water, ethers, alcohols, esters, ketones, nitriles, hydrocarbons, halogenated hydrocarbons and nitrated hydrocarbons (see, for example, U.S. Pat. No. 2,866,801). In order to overcome this difficulty, some suggestions have been made in the past. They include, for example, the method which comprises reacting a certain organic halide with an alkali metal cyanate in a strongly polar aprotic solvent such as dimethyl formamide (DMF), dimethyl sulfoxide (DMSO) or dimethyl sulfone (Japanese Patent Publication No. 4372/61 and U.S. Pat. Nos. 2,866,801 and 3,017,420) and the method which involves using a quaternary ammonium halide or a tertiary amine, such as tetraethylammonium iodide or trimethylamine, as a reaction catalyst (U.S. Pat. Nos. 2,866,802 and 2,866,803).

These methods, however, cannot be applied to the production of isocyanates from the corresponding tertiary alkyl halides in accordance with this invention. When a tertiary alkyl halide having a hydrogen atom at the carbon atom adjacent the tertiary carbon atom to which the halogen atom is bonded is heated in a polar solvent having a strong affinity for acids, such as dimethylformamide (DMF) and dimethylsulfoxide (DMSO), or in the presence of a tertiary amine and a quaternary ammonium salt, it readily undergoes dehydrohalogenation to become an olefin, and the desired isocyanate can scarcely be obtained.

Some methods are shown below which were suggested in the past to produce organic isocyanates from organic halides having a tertiary alkyl halide group and alkali metal cyanates or other cyanates.

(a) An organic halide is reacted with an alkali metal cyanate in a medium consisting of water and a solvent miscible with the organic halide with the aid of an interphase transferable catalyst such as n-cetyltrimethylammonium bromide (Chem. Abst. Vol. 84, 1976, 30650 p). Based on the fact that the alkali metal cyanate, one of the reactants, is scarcely soluble in common organic solvents but well soluble in water, and the organic halide, the other reactant, is well soluble in organic solvents but is scarcely soluble in water, this method uses as an interphase transferable catalyst a salt which in the form of halogen salt, is soluble in water but sparingly soluble in organic solvents, and in the form of cyanic acid salt, has an increased solubility in the organic solvents, such as $R_4NX$, $R_4PX$, $R_4AsX$ or $MX_nY_m$ (where R=alkyl or aryl radical, M=metal, $Y=R_3P$, $R_3PO$ or $R_3N$, and X is chlorine or bromine in the case of the halogen salt, and OCN— in the case of the cyanic acid salt), and causes the reaction to proceed with the aid of this catalyst.

Hence, in order for the interphase transferable catalyst to function, the presence of water in the reaction system is essential. However, when the starting material is a tertiary alkyl halide as in the present invention, the presence of water in the reaction system inevitably causes undesirable side reactions, such as the hydrolysis of the starting material to form a carbinol, the decomposition of the resulting isocyanate to form an amine, or the further reaction of the by-product amine with the isocyanate to form a disubstituted urea compound, and the intended isocyanate cannot be obtained in satisfactory yields.

(b) Another prior method comprises reacting the organic halide in an organic solvent with a cyanate soluble in the organic solvent, for example a quaternary ammonium salt, quaternary phosphonium salt, sulfonium salt, arsonium salt, large-ring heterocyclic compound complex or metal complex (Chem. Abst. Vol. 84, 1976, 30649 v). According to this method, cyanic acid salts soluble in organic solvents are used as reactants instead of the alkali metal cyanates which are substantially insoluble in organic solvents. These soluble cyanic acid salts are the same substances as the cyanic acid salt form of the interphase transferable catalyst used in method (a) described above. In this regard, methods (a) and (b) basically have a common technical concept. The method (b) cannot use alkali metal cyanates available at low cost, and requires the production of the cyanic acid salts which are soluble in organic solvents. The production of these compounds is not simple, and requires separate manufacturing equipment. Moreover, the effluent from the process of producing the cyanic acid salts contains large quantities of phosphorus compounds, amines, or heavy metals, and enormous amounts of labor and expenditure must go into the disposal of these unwanted inclusions.

It will be understood from the above description of the prior art that the production of organic isocyanates by the reaction of organic halides with cyanates, especially alkali metal cyanates, encounters difficulties, and the production of tertiary alkyl isocyanates by the reaction of tertiary alkyl halides with alkali metal cyanates, involves various difficulties and problems.

In view of the state of the art, the present inventors made various investigations about a method which can afford a tertiary alkyl isocyanate in a high yield by using the corresponding tertiary alkyl halide and an alkali metal cyanate such as sodium cyanate or potassium cyanate, which is readily available at low cost as an industrial material. These investigations led to the discovery that according to this invention, there is provided a commercially advantageous process for the production of a tertiary alkyl isocyanate such as tert-butyl isocyanate.

The present applicants previously found a new process for producing α,α-dimethylbenzyl isocyanate or its ring-substituted derivatives (U.S. Ser. No. 844,815 filed Oct. 25, 1977, now U.S. Pat. No. 4,130,577 issued Dec. 19, 1978). They developed this process, and accomplished the present invention.

The process for preparing the tertiary alkyl isocyanate in accordance with this invention comprises reacting the corresponding tertiary alkyl halide in a substantially anhydrous condition with an alkali metal cyanate in the presence of, as a catalyst, at least one salt selected from the group consisting of mineral acid salts or carboxylic acid salts of Zn, Fe, Sb, Sn and Co.

The tertiary alkyl halide as a starting material is a halide corresponding to the tertiary alkyl isocyanate of formula (i), (ii) or (iii) given hereinabove. Preferably R in these formulae is an alkyl group containing 1 to 3 carbon atoms. The tertiary alkyl halide should not contain in the molecule a substituent containing active hydrogen having high reactivity with the organic isocyanates, such as $-NH_2$, $-NHR$, $-COOH$, $-SO_3H$, $-OH$ or $-SH$. However, it may contain at least one aprotic substituent such as halogen or nitro on the primary or secondary carbon atom in the alkyl chain, and the aprotic substituents bonded to the primary or secondary carbon atom are not involved in the reaction. For example, 1,2-dichloro-2-methylbutane reacts with an alkali metal cyanate to give 1-chloro-2-isocyanato-2-methyl butane. In other words, only the halogen atom bonded to the tertiary carbon atom reacts with the alkali metal cyanate. Accordingly, a tertiary alkyl halide having two tertiary carbon atoms having a halogen atom bonded to each of them reacts with the alkali metal cyanate to give the corresponding diisocyanate represented by formula (ii) or (iii). The tertiary alkyl halide may contain in the molecule an aliphatic ring such as cyclohexane or cyclopentane.

Sodium cyanate and potassium cyanate are preferred as the alkali metal cyanate as the other starting material.

The ratio between the tertiary alkyl halide and the alkali metal cyanate is not particularly limited. Usually, the amount of the latter is 0.8 to 4 times, preferably 1 to 2 times, the stoichiometric amount of the former. Generally, the alkali metal cyanate is used in a somewhat excessive amount. If the amount of the alkali metal cyanate is too excessive, the yield of the desired product is reduced.

The catalysts used are mineral acid salts or carboxylic acid salts of the five metals described hereinabove. Examples of preferred salts include chlorides, bromides, sulfates, nitrates, formates, acetates, propionates, butyrates and naphthenates. It is not essential that the catalyst added to the reaction mixture be in a form soluble in the reaction mixture, and initially, it may be insoluble in the reaction mixture. The salts of zinc are most preferred.

The amount of the catalyst is not particularly limited, but if it is too small, a sufficient effect cannot be obtained. On the other hand, if it is too large, side reactions such as intramolecular dehydrogenation tend to be increased. Hence, the amount of the catalyst is generally 0.5 to 50 mole%, preferably 0.5 to 30 mole%, especially 1 to 10 mole%, based on the starting tertiary alkyl halide.

The reaction in accordance with this invention is carried out in a suitable organic solvent. Even in the absence of a solvent, the reaction proceeds by the aid of the catalyst. However, in the absence of solvent, the intramolecular dehydrohalogenation of the starting organic halide occurs markedly, and the final product cannot be obtained in good yields. Suitable organic solvents are aprotic solvents which do not form any salts or adducts with hydrogen halides.

Solvents containing active hydrogen such as water, alcohols, primary or secondary amines, carboxylic acids, sulfonic acid or mercaptan are not used in this invention. Those aprotic solvents which have high reactivity in dehydrohalogenation and form salts or adducts with hydrogen halides, such as dialkyl formamides (e.g., dimethyl formamide), dialkyl sulfoxides (e.g., dimethyl sulfoxide), pyridine, trialkyl phosphines or trialkyl phosphites, can also not be used in this invention.

The aprotic solvents which do not form salts with hydrogen halides include chlorinated aliphatic or aromatic hydrocarbons, esters, nitriles, nitro compounds, ketones and aliphatic or cyclic ethers.

Specific examples of these aprotic solvents are dichloromethane, chlorobenzene, dichlorobenzene, trichloroethylene, methyl formate, ethyl formate, propyl formate, butyl formate, methyl acetate, ethyl acetate, propyl acetate, butyl acetate, ethyl Cellosolve acetate, butyl Cellosolve acetate, 1,2-diacetoxyethane, γ-butyrolactone, phenylacetate, acetonitrile, propionitrile, succinonitrile, benzonitrile, tolunitrile, benzyl cyanide, β-methoxypropionitrile, nitromethane, nitroethane, nitropropane, nitrobenzene, nitrotoluene, acetone, methyl ethyl ketone, diethyl ketone, methyl isobutyl ketone, cyclohexanone, diethyl ether, dipropyl ether, dibutyl ether, tetrahydrofuran, 1,2-dimethoxyethane, ethyl Cellosolve methyl ether, 1,2-diethoxyethane, diethylene glycol dimethyl ether, diethylene glycol diethyl ether, dioxane, and anisole.

Non-polar solvents having a very low solubilizing power for the alkali metal cyanates, such as benzene, toluene and xylene, can also be used effectively.

The reaction in accordance with this invention should be carried out in a substantially anhydrous condition because the presence of water, as stated hereinabove, causes undersirable side-reactions such as the hydrolysis of the starting alkyl halide and reduces the yield of the desired alkyl isocyanate. However, in actual commercial operations, the starting materials, solvent or catalyst may inevitably contain very small amounts of water. In such a case, too, the amount of water should not exceed 0.5% by weight based on the amount of the entire reaction mixture. Experiment has shown that if the amount of water is larger than 0.5% by weight, the yield of the final product markedly decreases.

The reaction in accordance with this invention proceeds smoothly under relatively mild conditions, for example at a temperature of 0° C. to 200° C. The reaction temperature is chosen according to the type of the solvent or catalyst used. The preferred temperature is 50° C. to 100° C.

It has been found that practical effects, such as a further increase in yield or the termination of the reaction within a shorter period of time, can be obtained by causing a small amount of a promotor to be present in the reaction system of the present invention. Effective generally is the use of a small amount of formamide, a dialkyl formamide, a dialkylsulfoxide, a dialkylsulfone, a trialkyl phosphine, a trialkyl phosphite, a macrocyclic polyether, urea, an alkylurea, or an alkyl-, aryl- or heterocyclic amine such as imidazole. When the amount of the promotor is too large, the yield is reduced extremely, and therefore, the use of the promotor in an amount of more than 2 moles per mole of the main catalyst should be avoided. The preferred amount of the promotor is from 0.1 to 1.0 mole per mole of the main catalyst.

It is quite surprising that as stated hereinabove, when the carbon atom to which a halogen atom is bonded to tertiary, reaction with an alkali metal cyanate can give an isocyanate as in the present invention. The operating conditions and the results obtained in the process of this invention are of high utilitarian value, and the present invention is excellent for commercial application.

The following Examples further illustrate the present invention.

EXAMPLE 1

To 10 ml of 1,4-dioxane were added 30 millimoles of 98% sodium cyanate, 20 millimoles of tert-butyl chloride and 2 millimoles of zinc chloride, and with stirring, they were heated at 85° C. for 1.5 hours. After the reaction, the liquid layer was analyzed by gas chromatography. The results of the reaction (based on the tert-butyl chloride) were as follows:

Yield of tert-butyl isocyanate (tBI for short): 74.4 mole%

Conversion of tert-butyl chloride (tBC for short): 97.9 mole%

EXAMPLES 2 to 5

Example 1 was repeated except that each of the catalysts shown below was used instead of zinc chloride, and the reaction time was also varied as shown below. The results are shown in the following table.

| Example | Catalyst | Reaction time (hours) | Yield of tBI (mole %) | Conversion of tBC (mole %) |
|---|---|---|---|---|
| 2 | Cobalt | 4.7 | 56.3 | 87.3 |
| 3 | Stannic chloride | 4 | 52.7 | 80.8 |
| 4 | Ferric chloride | 2 | 33.9 | 98.4 |
| 5 | Antimony pentachloride | 4 | 31.6 | 99.1 |

EXAMPLE 6

To 10 ml of 1,4-dioxane were added 36 millimoles of 90% sodium cyanate, 2.25 moles of zinc chloride, 2.25 millimoles of formamide and 30 millimoles of tBC. They were reacted with stirring at 85° C. for 1.5 hours. The conversion of tBC was 98.1 mole%, and the yield of tBI was 84.9 mole%.

EXAMPLE 7

To 10 ml of 1,4-dioxane were added 24 millimoles of 90% sodium cyanate, 1.5 millimoles of zinc chloride, and 20 millimoles of tBC. They were reacted with stirring at 85° C. for 2 hours. The results were as follows:

Yield of tBI: 56.3 mole%

Conversion of tBC: 85.1 mole%

EXAMPLE 8

To 10 ml of ethylene glycol monoethyl ether acetate were added 36 millimoles of 90% sodium cyanate, 2.5 millimoles of zinc chloride, 1.3 millimoles of urea and 30 millimoles of tert-amyl chloride. They were reacted with stirring at 85° C. for 2 hours. The results were as follows:

Yield of tert-amyl isocyanate: 83.3 mole%
Yield of tert-amyl chloride: 97.6 mole%

EXAMPLE 9 (COMPARISON)

36 millimoles of 90% sodium cyanate, 30 millimoles of tBC, and 3 millimoles of zinc chloride were mixed with 10 ml of N,N-dimethyl formamide, and the mixture was reacted with stirring at 50° C. for 1 hour. But tBI was not formed. When the reaction was continued further for 1 hour at 85° C., the following results were obtained.

Yield of tBI: 3.3 mole%
Conversion of tBC: 24.9 mole%

EXAMPLE 10

15 millimoles of 98% sodium cyanate, 10 millimoles of tBC and 1 millimole of zinc chloride were mixed with 10 ml of m-xylene. The mixture was heated to 85° C., and stirred for 5 hours. The results were as follows:

Yield of tBI: 66.6 mole%
Conversion of tBC: 91.2 mole%

EXAMPLE 11

15 millimoles of 98% sodium cyanate, 10 millimoles of tBC and 0.5 millimole of basic zinc chloride were mixed with 1,4-dioxane. The mixture was heated to 85° C., and stirred for 2 hours. The results obtained were as follows:

Yield of tBI: 50.9 mole%
Conversion of tBC: 96.7 mole%

EXAMPLE 12

To 10 ml of acetonitrile were added 15 millimoles of 98% sodium cyanate, 10 millimoles of tBC and 2 millimoles of zinc fluoride. The mixture was reacted at 85° C. for 6 hours. The following results were obtained.

Yield of tBI: 41.1 mole%
Conversion of tBC: 72.5 mole%

EXAMPLES 13 to 16

To 10 ml of 1,4-dioxane were added 30 millimoles of 98% sodium cyanate and 20 millimoles of tBC, and the mixture was reacted at 95° using 2 millimoles of each of the catalysts shown below. The results are also tabulated below.

| Example | Catalyst | Reaction time (hours) | Yield of tBI (mole %) | Conversion of tBC (mole %) |
|---|---|---|---|---|
| 13 | Zinc bromide | 3 | 57.5 | 89.7 |
| 14 | Zinc sulfate | 1 | 46.0 | 97.0 |
| 15 | Basic zinc carbonate | 0.5 | 41.8 | 98.8 |
| 16 | Zinc acetate | 1 | 42.4 | 92.2 |

EXAMPLE 17

An autoclave was charged with 10 ml of ethyl acetate, 2.25 millimoles of zinc chloride, 1.78 millimoles of imidazole, 36 millimoles of 90% sodium cyanate, and 30 millimoles of tBC. The mixture was shaken at 90° C. for 1 hour, and the following results were obtained.

Yield of tBI: 83.5 mole%
Conversion of tBC: 97.9 mole%

EXAMPLE 18

An autoclave was charged with 10 ml of tetrahydrofuran, 1.5 millimoles of zinc chloride, 0.33 millimole of 1,4,7,10,13,16-hexaoxacyclooctadecane (trivial name: 18-crown-6), 36 millimoles of 90% sodium cyanate and 30 millimoles of tBC, and heated at 90° C. for 1.5 hours. The following results were obtained:

Yield of tBI: 78.7 mole%
Conversion of tBC: 98.7 mole%

EXAMPLE 19

To 10 ml of 1,4-dioxane were added 36 millimoles of 90% sodium cyanate, 2.25 millimoles of zinc chloride, 2.0 millimoles of dimethylformamide and 10 millimoles of 1,2-dichloro-2-methylbutane. They were heated to 85° C., and stirred for 3 hours. The following results were obtained.

Yield of 1-chloro-2-isocyanato-2-methylbutane: 57.3 mole%
Conversion of 1,2-dichloro-2-methylbutane: 83.3 mole%

What we claim is:

1. A process for preparing an alkyl isocyanate having the isocyanato group bonded to a tertiary carbon atom of the alkyl group, which comprises reacting the corresponding alkyl halide having the halogen atom bonded to the tertiary carbon atom of the alkyl group, with an alkyl metal cyanate in an organic solvent in a substantially anhydrous condition at a temperature between 0° C. and 200° C. in the presence of, as a catalyst, at least one salt selected from the group consisting of mineral acid salts or carboxylic acid salts of Zn, Fe, Sb, Sn and Co, said organic solvent being an aprotic solvent which forms no salt or adduct with a hydrogen halide.

2. The process of claim 1 wherein the reaction is carried out at a temperature between 50° C. and 100° C.

3. The process of claim 1 wherein the amount of the alkali metal cyanate is 0.8 to 4 times the stoichiometric amount of the alkyl halide.

4. The process of claim 1 wherein the amount of the alkali metal cyanate is 1 to 2 times the stoichiometric amount of the alkyl halide.

5. The process of claim 1 wherein the reaction is carried out under such a condition that the water content of the starting reaction mixture does not exceed 0.5% by weight.

6. The process of claim 1 wherein the amount of the catalyst is from 0.5 to 50 mole% based on the alkyl halide.

7. The process of claim 1 wherein the amount of the catalyst is from 0.5 to 30 mole% based on the alkyl halide.

8. The process of claim 1 wherein the amount of the catalyst is from 1 to 10 mole% based on the alkyl halide.

9. The process of claim 1 wherein the alkyl halide is tertiary butyl chloride, and the alkyl isocyanate is tertiary butyl isocyanate.

10. The process of claim 1 wherein the reaction is carried out in the copresence of at least one promotor selected from the group consisting of formamide, a dialkyl formamide, a dialkylsulfoxide, a dialkylsulfone, a trialkyl phosphine, a trialkyl phosphite, a macrocyclic polyether, urea, an alkyl urea, an alkyl amine, an aryl amine and a heterocyclic amine, in an amount of 0.1 to 1.0 mole per mole of the catalyst.

* * * * *